(12) United States Patent
Martens et al.

(10) Patent No.: US 9,468,460 B2
(45) Date of Patent: Oct. 18, 2016

(54) NEUROSURGICAL GUIDING TOOL

(75) Inventors: Hubert Cecile Francois Martens, Eindhoven (NL); Michel Gerardus Pardoel, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 159 days.

(21) Appl. No.: 13/126,475

(22) PCT Filed: Nov. 5, 2009

(86) PCT No.: PCT/IB2009/054913
§ 371 (c)(1),
(2), (4) Date: Apr. 28, 2011

(87) PCT Pub. No.: WO2010/055444
PCT Pub. Date: May 20, 2010

(65) Prior Publication Data
US 2011/0208225 A1 Aug. 25, 2011

(30) Foreign Application Priority Data
Nov. 12, 2008 (EP) .................................... 08168888

(51) Int. Cl.
*A61B 19/00* (2006.01)
*A61B 17/34* (2006.01)
*A61N 1/05* (2006.01)

(52) U.S. Cl.
CPC ........... *A61B 17/3403* (2013.01); *A61B 90/11* (2016.02); *A61B 2017/3409* (2013.01); *A61B 2017/3411* (2013.01); *A61N 1/0534* (2013.01); *A61N 1/0539* (2013.01)

(58) Field of Classification Search
CPC A61B 19/201; A61B 17/3403; A61B 90/11; A61B 2017/3409; A61B 2017/3411; A61N 1/0534; A61N 1/0539
USPC .................................................. 606/148, 130
See application file for complete search history.

(56) References Cited

U.S. PATENT DOCUMENTS

| | | | |
|---|---|---|---|
| 3,760,811 | A | 9/1973 | Andrew |
| 4,931,056 | A | 6/1990 | Ghajar |
| 5,052,396 | A | 10/1991 | Wedel |
| 5,069,206 | A | 12/1991 | Crosbie |
| 5,695,501 | A | 12/1997 | Carol |

(Continued)

FOREIGN PATENT DOCUMENTS

| | | |
|---|---|---|
| CN | 101066215 A | 11/2007 |
| DE | 202007001749 U1 | 7/2007 |

(Continued)

OTHER PUBLICATIONS

First Office Action dated Jan. 4, 2013 for Chinese Patent Application No. 200980145122.7.

(Continued)

*Primary Examiner* — Richard Louis
(74) *Attorney, Agent, or Firm* — Shumaker & Sieffert, P.A.

(57) ABSTRACT

The present invention regards a guiding tool for neurosurgery. The guiding tool comprises subunits and a holder. The subunits are arranged in the holder so that holes for guiding a probe are created in the interface between said subunits, which allows easy release of the probe. The invention further regards a system for guiding neurosurgery probes.

16 Claims, 5 Drawing Sheets

(56) References Cited

U.S. PATENT DOCUMENTS

| | | | |
|---|---|---|---|
| 5,954,687 A * | 9/1999 | Baudino | 604/48 |
| 6,413,263 B1 * | 7/2002 | Lobdill et al. | 606/129 |
| 7,033,326 B1 * | 4/2006 | Pianca et al. | 600/585 |
| 7,137,969 B1 * | 11/2006 | Mendez | A61B 17/3403 604/187 |
| 7,343,205 B1 | 3/2008 | Pianca | |
| 2003/0014097 A1 * | 1/2003 | Putz | A61F 7/12 607/113 |
| 2005/0234476 A1 * | 10/2005 | Whitmore et al. | 606/130 |
| 2008/0132987 A1 * | 6/2008 | Westlund et al. | 607/122 |
| 2008/0255583 A1 * | 10/2008 | Gielen | A61B 17/3403 606/130 |
| 2009/0312770 A1 * | 12/2009 | Kozai et al. | 606/129 |

FOREIGN PATENT DOCUMENTS

| | | |
|---|---|---|
| EP | 1852076 A1 | 11/2007 |
| EP | 2005892 A2 | 12/2008 |
| WO | 2005079903 A2 | 9/2005 |

OTHER PUBLICATIONS

Notice of Reasons for Rejection dated Dec. 18, 2013 for Japanese Patent Application No. 2011-535195.
Third Office Action dated Feb. 21, 2014 for Chinese Patent Application No. 200980145122.7.
EP Office action dated Feb. 17, 2014 for European Patent Application No. 09759805.6.

* cited by examiner

NEUROSURGICAL GUIDING TOOL

FIELD OF THE INVENTION

The present invention pertains to the field of neurotechnology. More particularly, the present invention pertains to the field of neurosurgery and a tool for guiding neurosurgical probes.

BACKGROUND OF THE INVENTION

Within the field of neurotechnology, deep brain stimulation (DBS) is a surgical treatment involving the implantation of a medical device called a deep-brain stimulator, which sends electrical impulses to specific parts of the brain. DBS in certain brain regions has provided remarkable therapeutic benefits for otherwise treatment-resistant disorders such as chronic pain, Parkinson's disease, tremor and dystonia. Despite the long history of DBS, its underlying principles and mechanisms are still not clear. DBS directly changes brain activity in a controlled manner. Unlike lesioning techniques, its effects are reversible. Furthermore, DBS is one of only a few neurosurgical methods that allow blinded studies.

In principle, the deep brain stimulation system comprises two components: the implanted pulse generator (IPG), and the probe. The IPG is a battery-powered neurostimulator that sends electrical pulses to the brain to interfere with neural activity at the target site. The IPG is typically encased in e.g. a titanium housing. The probe consists of about 10-40 cm long wires and a plurality of electrodes. The wires connect the IPG to the electrodes, which are located at the distal end of the probe. The IPG may be calibrated by a neurologist, nurse or trained technician to optimize symptom suppression and control side effects.

DBS probes are placed in the brain according to the type of symptoms to be addressed. All components are surgically implanted inside the body. The typical procedure is performed under local anaesthesia, where a hole is drilled in the skull and the electrode is inserted with feedback from the patient for optimal placement. The right side of the brain is stimulated to address symptoms on the left side of the body and vice versa.

In stereotactic neurosurgical procedures one often needs to target a small structure in the delicate brain tissue. Frequently, the precise location is not known during the surgical planning stage, either because it is poorly visible on anatomic patient images, such as MRI, or because specific features of interest, such as functionality, cannot be visualized directly by existing medical imaging techniques.

To cope with this uncertainty, a number of parallel trajectories towards the presumed target brain area are often sampled. This is especially important during deep brain stimulator implantation. In this case a tool called Ben's gun, well known to a person skilled in the art, is used to guide five probes through holes along parallel paths to the presumed target area. FIG. 1 is showing top view of a guiding tool 10, currently used in Ben's gun, with five holes 13, shaped as a cross formed by two rows of three holes, with one hole in the centre. The centre hole represents the position, from which the probe has to enter the tissue in a z-direction in order to end up in the target area. The location of the target area, and thus the positioning of the centre hole, is based on MRI scans, and calculated by software when planning the insertion of a probe. However, in order to allow for slight miscalculations, the other four holes, placed around the centre hole at a distance of about 2 mm, allow adjustment of the positioning of the probe in a x- or y-direction at the time when the application is performed. Thus, a correction of 1-2 mm in lateral-medial and posterior-anterior directions can be made with respect to the central path. In DBS procedures Ben's gun is positioned in a so-called micro-drive system, well known to a person skilled in the art, which is used to accurately guide the probes into the brain tissue.

FIG. 2 is showing application of a probe 11 through a cross section of a guiding tool 10 according to prior art, such as Ben's gun. This is applicable when the probe is used temporarily, i.e. not when the probe is to be left inside the tissue, such as in deep brain stimulation (DBS). FIG. 2 A is showing the probe position before entering the tissue. The arrow marks the downward movement of the probe. FIG. 2 B is showing how to extract the probe from the tissue after use. The arrow marks the upward movement of the probe.

FIG. 3 is showing another way of applying a probe 11 through a guiding tool 10 according to prior art, such as Ben's gun. This is applicable when the probe is to be applied and left in the tissue. FIG. 3 A is showing the probe position before entering the tissue. The arrow marks the downward movement of the probe. FIG. 3 B is showing the probe in position inside tissue. FIG. 3 C is showing how to extract the probe from the tissue after use. The arrow marks the sideway motion with which the probe is pulled through the hole, where after the guiding tool 10 may be removed.

The layout of Ben's gun is such that probes guided into the tissue can only be removed from Ben's gun by pulling them back out the way they were inserted. The probe may also be pulled all the way through Ben's Gun. When inserting chronic probes, which is the case in DBS, the only option is to pull probe all the way through Ben's gun which may induce mechanical forces on the probe, with the risk of displacement of the probe in the (deep) brain tissues. Also, the pulling through requires the probe's diameter along its full length to be smaller than the diameter of the holes of Ben's gun. This limits the functionality of the probe at its proximal size since the size of any connector, electronics, or other component that is attached to the proximal end of the probe is constrained by the diameter of the guide.

Hence, an improved tool for guiding neurosurgical probes, allowing for increased flexibility, cost-effectiveness, safety and user friendliness would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems e.g. by providing a guiding tool for neurosurgery.

In an aspect a guiding tool for insertion of a probe into tissue is provided. The guiding tool comprises a number of subunits, wherein each subunit along its edge is provided with an indentation, each subunit having a shape configured to fit in a predetermined configuration of the number of subunits, wherein the configuration comprises a number of holes formed by the indentations of the number of subunits and extending through the configuration.

In another aspect a system comprising a microdrive and a guiding tool according is provided, wherein the guiding tool, in use, is placed in the microdrive for enabling insertion of a probe into tissue.

The separate subunits of the guiding tool allow dismantling of the guiding tool after the probe has been guided into place. This is advantageous since the probe does not have to be drawn all the way through the tool. Thus, mechanical forces are not induced on the probe and the risk of displacement of brain tissues decreases. Also, the dismantling of the guiding tool also allows part of the probe diameter to be larger than the diameter of the holes of the guiding tool.

Other embodiments and advantages will be disclosed in the following.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Figure 1:
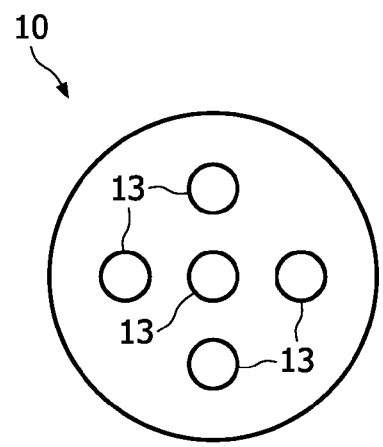
FIG. 1 is showing a top view of an illustration of a guiding tool according to prior art, called Ben's gun.
Figures 2A, 2B:
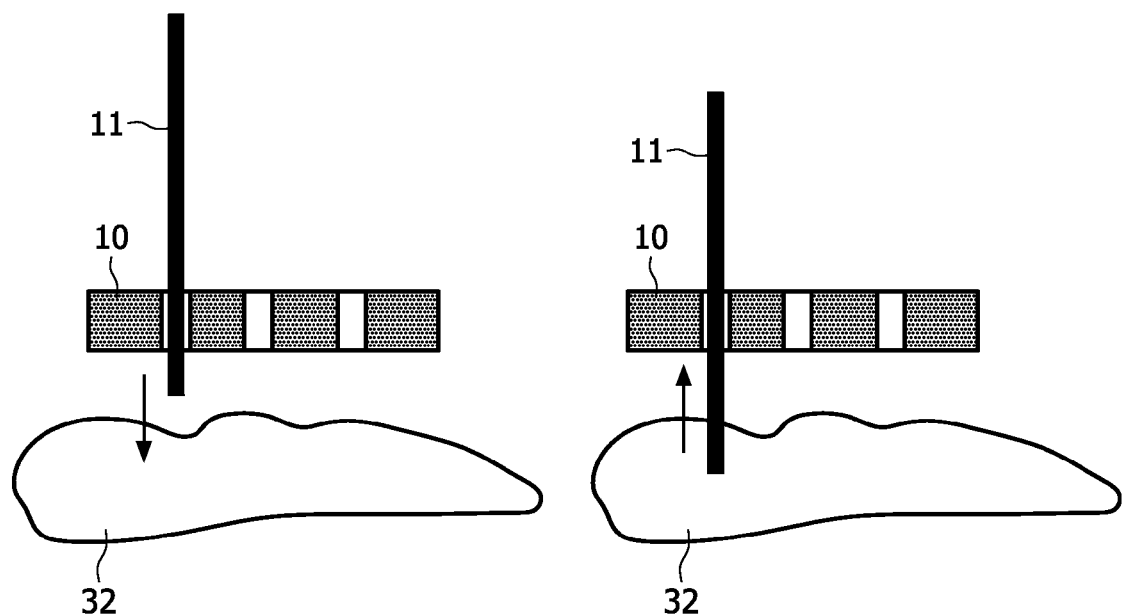
FIG. 2 is showing a cross-sectional side view of the application of a probe with a guiding tool according to prior art.
Figure 3A:
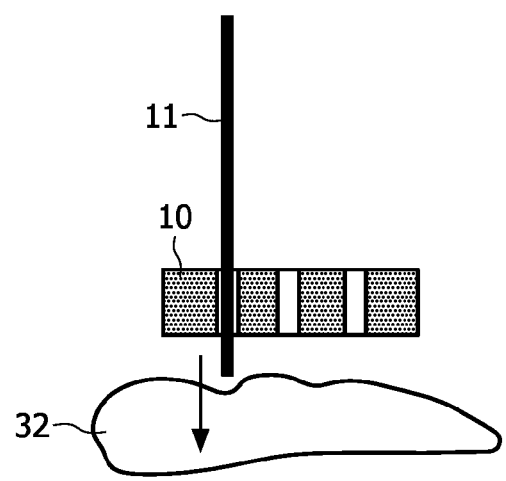
FIG. 3 is showing a cross-sectional side view of the application of a probe with a guiding tool according to prior art.
Figure 3B:
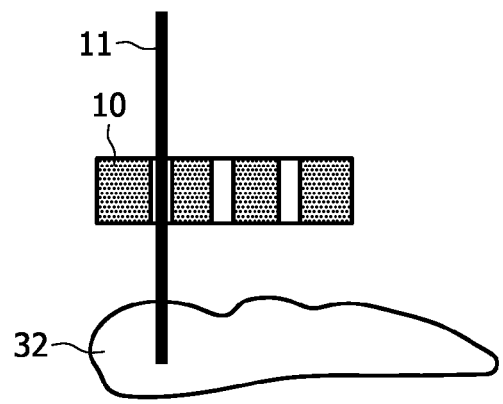
Figure 3C:
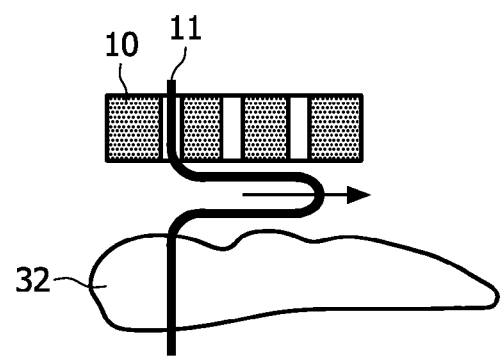
Figure 4:
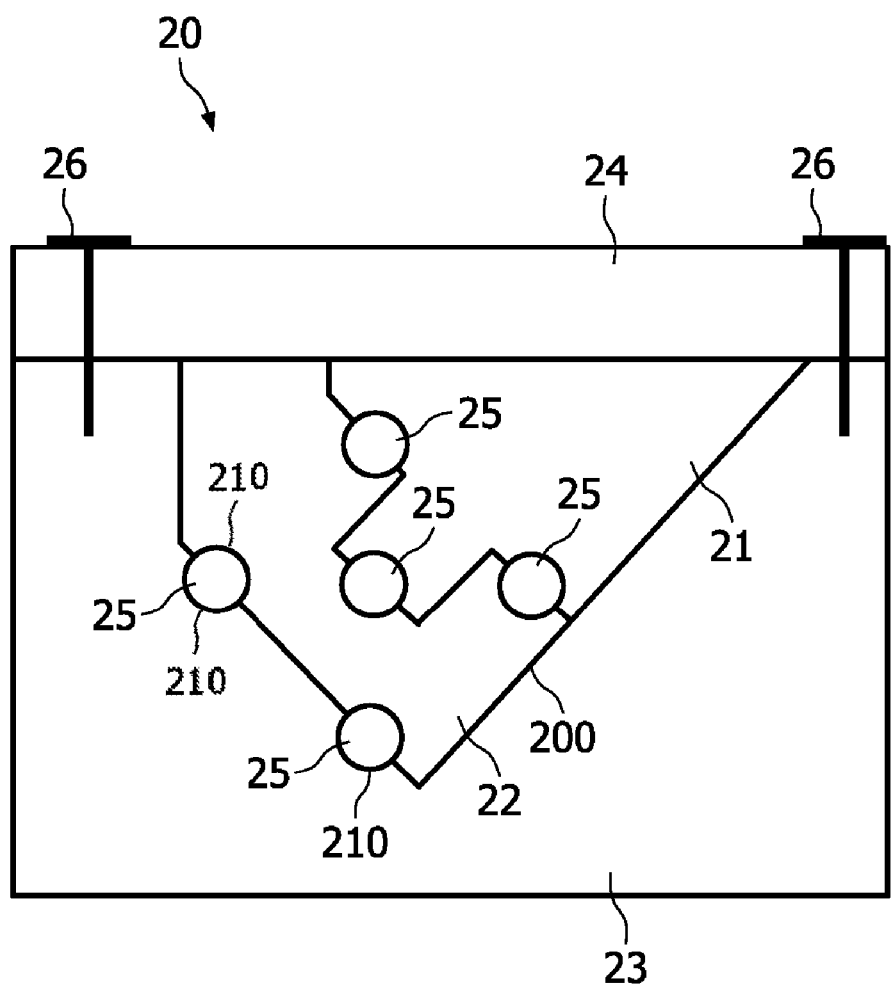
FIG. 4 is a perspective view of a guiding tool according to an embodiment.

In an embodiment, according to FIG. 4, a guiding tool 20 for guiding a probe into tissue is provided. The guiding tool 20 comprises a number of subunits 21,22,23, wherein the number of subunits may be mounted in a holder 24 in a configuration creating a plate with a number of holes 25 in the interface 200 between the subunits and extending straight through the plate. Each subunit has a shape configured to fit in the configuration of the number of subunits. The interface is the surface through which the subunits are in contact with each other. Each hole 25 has a size suitable for accommodating and/or guiding the insertion of a probe. The probe may be any kind of probe, but a deep brain stimulation (DBS) probe is preferred.

In an embodiment, each subunit is provided with at least one indentation 210, extending through the material of the subunit, positioned along the edge of each subunit, such that when two or more the subunits are positioned in the holder, the indentation of each subunit together with the indentation of another subunit, form a hole 25 in the interface 200 between the subunits 21, 22, 23, extending through the plate. The subunits are constructed such that their edges are fitting together, creating a tight interface between the subunits. Thus, if indentations are placed along the edge of two subunits otherwise configured to fit together creating an interface without space in between, the indentations may coincide thus creating a hole.

In an embodiment, the indentations 210 extending through the material of the subunit, are positioned along the edges of two subunits, the subunits being configured to fit together creating an interface 200, and the positioning is done in such a way that the indentations 210 coincide, a hole 25 is formed between the subunits, when the subunits are placed with the edges together, forming an interface between them. Depending on the configuration and number of subunits, and the configuration and number of indentations, a wide variety of plates may be created, with different number of holes, such as one, two, three, four, five, six, seven, eight, nine and ten holes, preferably five holes, the holes being configured in any way that facilitates insertion of a probe, preferably five holes positioned along two lines forming a cross, with three holes in each line.

Holder 24

The holder 24 may be any kind of piece, part, plate, cover, clasp, grip, hold, clinch, band, etc. suitable to hold together the subunits. In an embodiment according to FIG. 4, the holder 24 is a rectangle configured to fit tightly to the subunits 21, 22, 23. The holder 24 and the arrangement of subunit may be mounted together by means of an attachment means 26, under which influence the holder 24 may hold together the subunits 21, 22, 23. This will be further described below.

Attachment Means

The attachment means 26 may comprise any kind of screw, nail, clasp, tape, adhesive, riveter, etc. configured to fasten the holder so that the holder is holding together the subunit arrangement. FIG. 4 illustrates the holder 24 and three subunits 21, 22, 23 mounted together using the attachment means.

In an embodiment, the attachment means 26 are screws. The holder may hold together the subunits by pressure forces created between the subunits and the holder by the attachment means. When their interfaces are pressed against each other, frictional forces act to keep them in the plate configuration. In an embodiment, the holder is a plate equal in length and thickness to the plate created by the subunits. The attachment means, such as screws, may be applied in relation to the holder, such as running through it, in a direction parallel to the surface of the plate where through the holes are situated. The attachment means may then be attached in the subunits, which in case the attachment means are screws, create a pressure between the holder and the subunits when the screws are tightened.

Probe

In an embodiment the guiding tool 20 is utilized to accommodate and/or to guide a probe. The probe may be a probe suitable for deep brain stimulation. Commonly, a deep brain stimulation probe comprises a wire and stimulating sites, such as electrodes, for chronic insertion into the human brain. When inserting a DBS probe, also referred to as a chronic probe, a number of measurement electrodes or probes are also used. They are initially inserted in and around the pre-calculated target area and are used to initially stimulate the tissue to determine a site in which the chronic probe should be inserted. The measurement probe positioned the chosen site is then replaced with a chronic DBS probe.

The number of holes in the guiding tool may be varied to accommodate the desired number of measurement probes.

In a practical implementation, the guiding tool when assembled may comprise five holes formed by the indentations of the subunits. To determine a suitable position of the chronic probe, first five measurement electrodes are guided through the five holes into the tissue. All five measuring electrodes measure the neural activity. The central position of the guiding tool represents the position wherein a probe should be placed to end up in the calculated target area after insertion into tissue. A micro drive system, well known to a person skilled in the art, enables a range in z-direction, which is the desired direction of probe insertion, of the five measurement electrodes. After these measurements stimulation pulses are applied to all five measurement electrodes to determine the patient's reaction. Based on the neural measurements and the patient's reaction one of the five positions is chosen to be the best position to insert the chronic probe. This measurement electrode is removed. The other four measuring electrodes are remaining in position in order to keep the brain tissue in position and allow guiding during positioning of the chronic probe. Then, the chronic probe is inserted. The guiding tool may be disassembled to release the four remaining measurement electrodes and the chronic probe. The four measurement electrodes are then removed and the guiding tool used to position the chronic probe is disassembled to release the probe.

Subunits

The number of subunits may be any number, such as two, three, four, five, six, seven, eight, nine or ten. Preferably, the number of subunits is one more than the number of holes created by the indentations. Thus, by having one more subunit than holes, it is possible to individually open each hole by sequentially removing a subunit which is described in more detail below. The form of the subunits may be any form, as long as they are configured to fit together forming interfaces between each other, when placed next to each other, which interfaces substantially have a tight fit, i.e. no space between the subunits.

Indentations

The number of indentations may be any number, such as two, three, four, five, six, seven, eight, nine, ten, eleven, twelve, thirteen, fourteen, fifteen, sixteen, eighteen, nineteen or twenty.

Preferably, the number of indentations is twice the number of holes formed when placing the subunits next to each other, allowing the indentations to coincide. The indentations may be formed as parts of any geometrical structure, such as, parts of round, rectangular, squared, triangular, pentagonal, hexagonal, septagonal or octagonal, extending straight through the material of the subunit of the indentation. Preferably, the indentations are arc shaped parts of a circle and most preferably, the indentations are arc shapes, less than 180° of a circle.

The subunits may have one or more indentations. An indentation may be placed anywhere along the edge of the subunit, but preferably, an indentation is placed in such way that an indentation on a first subunit coincides with an indentation on a second subunit, when the first and second subunit are placed next to each other, thus forming an interface. Most preferably, the indentations of the subunits are placed in such away that when the subunits are arranged adjacently, e.g. in the holder, form a hole extending straight through the subunit arrangement.

Figure 5:
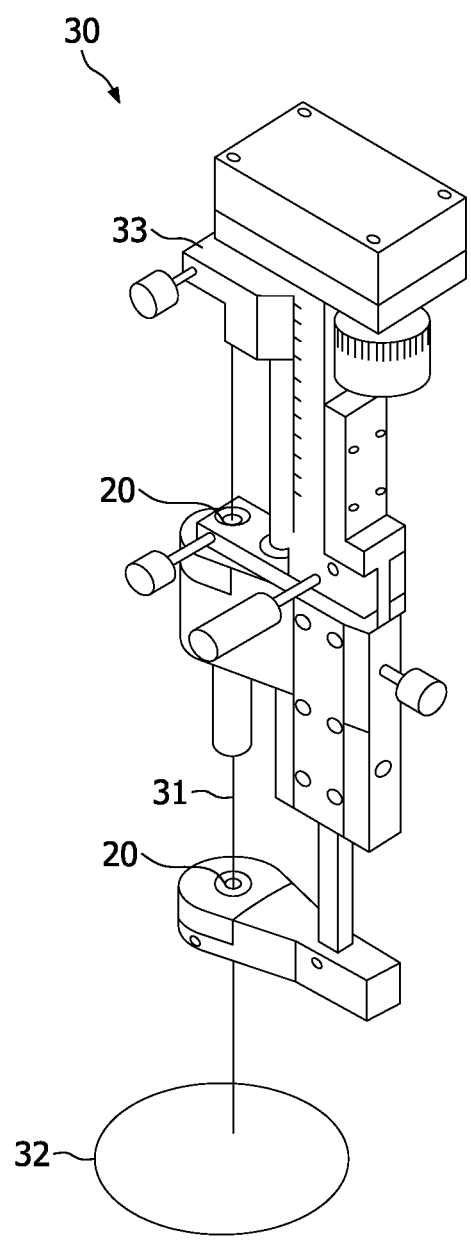
FIG. 5 is a an illustration of an instrument setup comprising the guiding tool according to an embodiment.

In an embodiment according to FIG. 5, the guiding tool 20 is mounted in an instrument setup 30 for insertion of a probe 31 into tissue 32. The probe 31 is fastened in the sledge 33 of the tool. The instrument setup 30 may be a well known micro drive system, but other kinds of setups are also possible. As previously stated, five measurement electrodes may be placed in the five respective holes of the guiding tool during the insertion procedure. The central position of the guiding tool is aligned along the z-direction of the calculated target, the z-direction being marked by the black line in FIG. 5. All five measuring electrodes measure the neural activity. A microdrive enables a range in z-direction of the five electrodes. The five measuring electrodes may be placed in the five respective holes to a certain depth determined by previous MRI scanning and calculations. This depth is approximately 10 mm before target position in z-direction. Now, the five measuring electrodes may be clamped to the sledge of the tool. By actuating the microdrive, such as by hand, by lead screw etc. the sledge is moved and so the z-position of the five measuring electrodes can be changed within a certain range, such as approximately +/−20 mm. This is needed to be able to find the most optimal position for stimulation. The working principles of all microdrive systems on the market are about the same. The five measuring electrodes are clamped to a slider, which can be moved by a lead screw and thus adjusted. The microdrive may be attached to the skull of the patient by a head-frame and a stereotactic frame, which is well known to a person skilled in the art.

The instrument setup work by positioning the probe 31 between several guiding tools 20, such as two, three, four, five and six guiding tools.

In an embodiment according to FIG. 5, the probe 31 is positioned between two guiding tools 20 in an Medtronic microdrive system, the guiding tools are positioned in a distance being smaller than the length of the probe, but great enough to stabilize the entire length of the probe from movements in a direction perpendicular to the length of the probe. Preferably, such distance is 15 cm. This keeps the probe 31 straight during insertion, since the probe at two instances, placed in different ends along the probe length, is stabilized from movements in a direction perpendicular to the length of the probe. The probe is in one end fastened in the sledge 33 of the microdrive system and has the other end positioned towards brain tissue 32. Moving the sledge towards the brain tissue thus creating a downward pressure on the probe, which causes the probe to move through the tissue 32 in the z-direction. The guiding tools 20 prevent the probe from moving in the plane vertical to the z-direction, i.e. the x- and y-directions.

Before insertion of the chronic DBS probe or the measuring probes, the guiding tool is placed in a micro drive system, well known to a person skilled in the art. Then, each probe is guided through a hole in the guiding tool and inserted with the micro drive system. When the probe is in position, the number of subunits together allows dismantling of the guiding tool. The probe may then be released without having to draw the probe all the way through the guiding tool. This is advantageous since mechanical forces are not induced on the probe, which decreases the risk of displacement of brain tissue. Also, the dismantling of the guiding tool also allows part of the probe diameter to be larger than the diameter of the holes the guiding tool.

In an embodiment, according to FIG. 6, a guiding tool 20 with six subunits and five holes is provided. By having one more subunit than holes, it is possible to individually open each hole by sequentially removing a subunit, which is shown in FIGS. 6 A-F. FIG. 6 A is showing the guiding tool with all the subunits assembled. The subunits together form a plate with five holes extending through the plate.

Each subunit also has means, such as holes, for receiving the attachment means attaching the holder to the subunits.

Figure 6A:
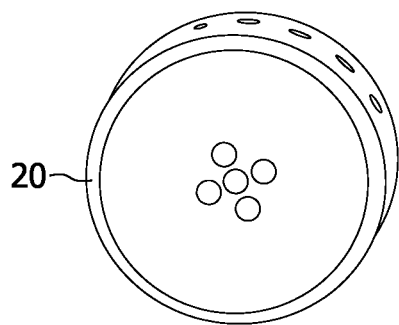
FIG. 6 is a perspective view of a guiding tool according to an embodiment.
Figure 6B:
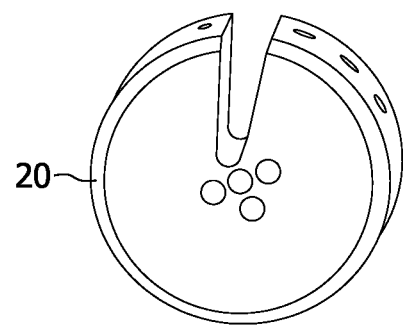
Figure 6C:
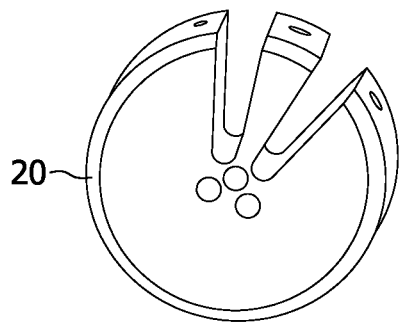
Figure 6D:
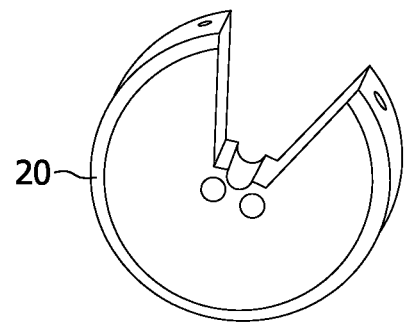
Figure 6E:
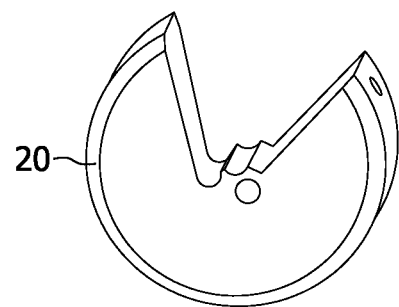
Figure 6F:
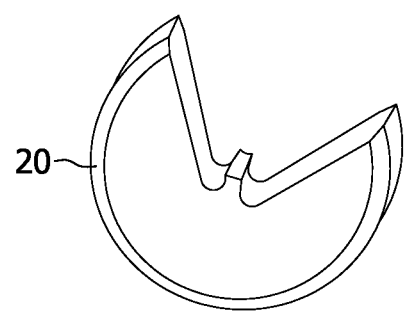

In an embodiment the subunits are held together by the holder 24 without the subunits having means for receiving the attachment means. One of the subunits, shown in FIG. 6F is the so-called base part, which always remains in position, i.e. fixed to the slider of the micro drive and onto which the other subunits are assembled by pressure forces created from the holder.

FIG. 6 B is showing the guiding tool with one subunit detached. Thereby, one of the holes is opened, so that a probe extending through the hole may be released by moving the guiding tool in a direction perpendicular to the axis of the probe. FIG. 6 C is showing the guiding tool with two subunits detached. Thereby, another hole is opened, so that a probe extending through the hole may be released by moving the guiding tool in a direction perpendicular to the axis of the probe. FIG. 6 D is showing the guiding tool with three subunits detached. Thus, yet another hole is opened, so that a probe extending through the hole may be released by moving the guiding tool in a direction perpendicular to the axis of the probe. FIG. 6 E is showing the guiding tool with four subunits detached. A further hole is opened, so that a probe extending through the hole may be released by moving the guiding tool in a direction perpendicular to the axis of the probe. FIG. 6 F is showing the guiding tool with five subunits detached. The result is that the last hole is opened, so that a probe extending through the hole may be released by moving the guiding tool in a direction perpendicular to the axis of the probe.

The guiding tool may be made of a number of materials, such as steel, aluminium, titanium or a composite, such as carbon-fibre enforced polymer composite. Preferably, the guiding tool is made of titanium, since titanium is well known in the medical world of implants, because of its outstanding bio-compatible properties and its outstanding mechanical properties. Titanium is well accepted within the medical field and is approved by the FDA as material for medical implants.

The guiding tool may have the following dimensions. The thickness or height of the guiding tool may be between 5 and 10 mm thick, preferably 10 mm. A thicker the guiding tool may provide better guiding behaviour. The width of the guiding tool may be 5 cm, but other sizes are also possible.

In an embodiment, each subunit is between 5 and 10 mm thick, however smaller or larger thickness is equally possible.

The size of the indentations or holes may be between 1 mm and 2 mm. In case the holes are circles, the diameter of the holes may be between 1 and 2 mm, preferably 1.8 mm. In case the holes have another geometrical shape, the size of the holes about the same as the abovementioned diameters.

An advantage with this is that the subunits are easily detachable from the probes, since the indentations 210 of the subunits, when the subunits are detached, are as wide as possible along the edges of the subunits.

In an embodiment, the subunits are configured so that there is only one possible way to fit the subunits in the holder, depending on the shape of the subunits and the holder. An advantage with this is that it is easy to assemble the guiding tool after it has been dissembled.

In an embodiment, at least one subunit has an edge, which is perpendicular to the cordas of the holes, in a point taken 90° from the interface between the subunits. An advantage with this is that a path is created by one of the subunits, along which the other subunits may be slid into place when assembling or dismounting the plate. This allows easy assembling or dismounting.

In another embodiment, a device is disclosed. The device is configured to form a number of subunits, having indentations, wherein the indentations are positioned on the subunits in such way that the indentations coincide when the subunits are placed next to each other, thus forming holes.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A guiding tool for guiding a deep brain stimulation probe into tissue, the guiding tool comprising: a plurality of subunits, each of the plurality of subunits having an indentation along an edge; and a holder configured to hold together the plurality of subunits, wherein the plurality of subunits are configured to be mounted in the holder to form a guiding tool including a plurality of holes, the plurality of holes including a central hole and two or more holes spaced around the central hole such that the central hole is generally in a center of the plurality of holes, each of the plurality of holes being formed around a complete perimeter by only two of the indentations, wherein the tool is configured to receive a distal end of the probe through at least one hole of the plurality of holes to guide the distal end of the probe into the tissue to implant the distal end of the probe while the probe is disposed within the at least one hole, and wherein the plurality of subunits are configured to be dismantled from the deep brain stimulation probe while the distal end of the deep brain stimulation probe is implanted into the tissue and while the probe is disposed within the at least one hole without drawing the deep brain stimulation probe through the at least one hole of the plurality of holes to remove the probe from within the at least one hole.

2. The guiding tool of claim 1, wherein the number of the plurality of subunits is less than a number of the plurality of holes.

3. The guiding tool of claim 1, wherein the number of the plurality of holes is five.

4. The guiding tool of claim 1, wherein the number of the plurality of subunits is three and the number of the plurality of holes is five.

5. The guiding tool of claim 1, wherein the plurality of holes includes a first row including two of the plurality of holes, a second row including one of the plurality of holes, and a third row including two of the plurality of holes.

6. the guiding tool of claim 1 further comprising at least one deep brain stimulation probe configured to be drawn though at least one the plurality of holes.

7. The guiding tool of claim 1, wherein each of the plurality of subunits has a different shape.

8. A guiding tool for guiding a deep brain stimulation probe into tissue, the tool comprising: a plurality of subunits, each of the plurality of subunits having an indentation along an edge; and a holder configured to hold together the plurality of subunits, wherein the plurality of subunits are configured to be mounted in a holder to form a guiding tool including a plurality of holes, the plurality of holes including a central hole and two or more holes spaced around the central hole such that the central hole is generally in a center of the plurality of holes, a number of the plurality of subunits being more than a number of the plurality of holes, wherein the tool is configured to receive a distal end of the probe through at least one hole of the plurality of holes to guide the distal end of the probe into the tissue to implant the distal end of the probe while the probe is disposed within the at least one hole, and wherein the plurality of subunits are configured to be dismantled from the deep brain stimulation probe while the distal end of the deep brain stimulation probe is implanted into the tissue and while the probe is disposed within the at least one hole without drawing the deep brain stimulation probe through the at least one hole of the plurality of holes to remove the probe from within the at least one hole.

9. The guiding tool of claim 8, wherein the number of the plurality of subunits is six and the number of the plurality of holes is five.

10. The guiding tool of claim 8, wherein removing one of the plurality of subunits from a remainder of the plurality of subunits opens only one of the plurality of holes.

11. The guiding tool of claim 6, wherein the at least one deep brain stimulation probe is a chronic deep brain stimulation probe.

12. The guiding tool of claim 1, wherein the holder and the plurality of subunits are mounted together using an attachment means, wherein the attachment means is configured to apply a pressure between the holder and the plurality of subunits to hold the holder and the plurality of subunits together.

13. The guiding tool of claim 1, wherein the plurality of subunits are configured such that there is only one possible way to fit the plurality of subunits in the holder to form the guiding tool.

14. The guiding tool of claim 1, wherein the plurality of subunits are configured to be removed from the deep brain stimulation probe without having to slide the deep brain stimulation probe through the guiding tool.

15. The guiding tool of claim 1, wherein the plurality of subunits are configured to allow a diameter of part of the deep brain stimulation probe to be larger than a diameter of one of the plurality of holes.

16. The guiding tool of claim 8, wherein the holder and the plurality of subunits are mounted together using an attachment means, wherein the attachment means is configured to apply a pressure between the holder and the plurality of subunits to hold the holder and the plurality of subunits together.

* * * * *